United States Patent
Rajsharad et al.

(10) Patent No.: US 8,123,849 B2
(45) Date of Patent: Feb. 28, 2012

(54) AQUEOUS FILM COATING COMPOSITION CONTAINING SODIUM ALGINATE AND PREPARATION THEREOF

(75) Inventors: Chetan Rajsharad, Mumbai (IN); Shivaji Kamble, Mumbai (IN); Suresh Pareek, Mumbai (IN)

(73) Assignee: Ideal Cures Pvt. Ltd., Mumbai (IN)

( * ) Notice: Subject to any disclaimer, the term of this patent is extended or adjusted under 35 U.S.C. 154(b) by 765 days.

(21) Appl. No.: 12/095,412

(22) PCT Filed: Jan. 31, 2006

(86) PCT No.: PCT/IN2006/000034
§ 371 (c)(1),
(2), (4) Date: May 29, 2008

(87) PCT Pub. No.: WO2007/063553
PCT Pub. Date: Jun. 7, 2007

(65) Prior Publication Data
US 2008/0312345 A1     Dec. 18, 2008

(30) Foreign Application Priority Data
Nov. 29, 2005 (IN) .......................... 1479/MUM/2005

(51) Int. Cl.
*C09D 105/04* (2006.01)
*C08L 5/04* (2006.01)
*A61K 9/34* (2006.01)

(52) U.S. Cl. ............... 106/205.01; 106/205.72; 424/464; 424/485

(58) Field of Classification Search ............. 106/205.01, 106/205.72; 424/464, 485
See application file for complete search history.

(56) References Cited

U.S. PATENT DOCUMENTS

| | | |
|---|---|---|
| 6,267,808 B1 | 7/2001 | Grillo et al. |
| 6,274,162 B1 | 8/2001 | Steffenino et al. |
| 6,468,561 B1 | 10/2002 | Grillo et al. |
| 6,699,315 B2 | 3/2004 | Augello et al. |
| 2003/0072731 A1 | 4/2003 | Gulian et al. |

*Primary Examiner* — David M Brunsman
(74) *Attorney, Agent, or Firm* — Merchant & Gould P.C.

(57) ABSTRACT

A coating composition comprising sodium alginate and plasticizer, optionally detackifying agents, opacifers and colorants. The coating composition of the present invention may be applied to a pharmaceutical and veterinary tablet, caplets, pellets, granules, neutraceuticals, food, confectionery, seeds, animal feed, fertilizers and pesticide tablets and provides an elegant, glossy, prompt release coating which does not retard the release of active ingredients from the coated substrate.

23 Claims, No Drawings

AQUEOUS FILM COATING COMPOSITION CONTAINING SODIUM ALGINATE AND PREPARATION THEREOF

This application is a 371 filing of PCT/IN2006/000034, filed Jan. 31, 2006.

FIELD OF THE INVENTION

This invention relates to the field of aqueous film coating of pharmaceutical substrates, veterinary substrates, nutraceutical products confectionery products, fertilizers, seeds and pesticides. Pharmaceutical substrates include tablets, caplets, pellets, granules, powders and the like. It is specifically concerned with providing an elegant, glossy, prompt release coating of the substrate which, is readily dispersed in aqueous media, and when applied as a coating and ingested by, for example, a human, does not retard the release of active ingredients from the coated substrate. The coating compositions of the present invention contain sodium alginate as the film former and optionally plasticizers. Other excipients, which maybe included in the coat, include detackifying agents, opacifiers, colorants, flavors, sweeteners and preservatives.

BACKGROUND OF THE INVENTION

Currently, most commercially available edible coatings utilize a synthetic cellulosic polymer such as hydroxypropylmethylcellulose (HPMC). Other synthetic film-formers, which are commonly used, include ethylcellulose, methylcellulose, polyvinylpyrrolidone, and polydextrose. The foregoing are usually used in combination with other ingredients including fillers, for example, lactose or maltodextrin; plasticizers, such as polyethylene glycols, dibutyl sebacate, and triethyl citrate; surfactants; and often coloring materials such as a food dye or pigment, including opacifiers such as titanium dioxide and the like. A particular disadvantage of coatings based primarily on HPMC is that the coating may harden over time and therefore increase tablet disintegration times. An increase in disintegration time delays the bioavailability of the active ingredient at least in proportion to the increase in disintegration time. Many other agents commonly used in coating compositions are also known to delay release of pharmaceutical agents, such as enteric coatings which use polymeric film forming materials which are insoluble in water, or gastric fluid some of these being specifically selected to by-pass both the stomach and small intestine and provide colonic release.

U.S. Pat. No. 6,267,808 discloses bright white film-coating compositions, which are dextrose based, and comprise an auxiliary film-former. The primary film-former of the invention claimed is dextrose. The auxiliary film-former may belong to a diverse class of agents such as PVP, HPMC, and dextrin's modified starches, gums, alginates, lactose, tapoica and PVA. The function of the auxiliary film-former is to enhance the strength of the film-coat by preventing the cracking of the primary film coat and to prevent edge wear/chipping of the coated substrate.

U.S. Pat. No. 6,274,162 describes elegant film coating systems comprising a primary film former, the primary film former comprising low bloom strength gelatin, or hydroxyethyl cellulose, or a combination thereof and a secondary film former, or a plasticizer, or a surfactant, or a glidant, or a suspension aid, or a colorant, or a flavorant, or a combination thereof. The secondary film former maybe sodium alginate, sodium carboxymethlylcellulose, pectin, gelatin, propylene glycol alginate, metlhylcellitlose, polydextrose, or combinations thereof.

U.S. Pat. No. 6,468,561 describes coatings comprising a polydextrose as a primary film-former and a secondary film-former comprising sodium alginate or propylene glycol alginate. The advantages of using a polydextrose based coating include the excellent film coat obtained possessing excellent adhesive qualities coupled with good organoleptic properties, that are low calorie and non-cariogenic in nature.

In the preparation of a coating formulation to be sprayed, the film former is usually dissolved or dispersed in a solvent, for example, water, along with the other ingredients of the formulation. In aqueous systems, since many polymers require significant time to become fully hydrated, the coating formulation must frequently be prepared in advance of the time it is to be applied to the tablets. A common procedure is to prepare these coating formulations the day preceding the coating operation in order to assure adequate hydration of the polymers used in them. In this present invention it is eventually found that polymer hydration required is as low as quarter an hour only.

The coatings of this invention meet U.S. Pharmacopoeia standards for rapid or immediate dissolution (U.S.P. monograph 23) of active ingredients from tablets or other solid dosage forms coated with them. They provide prompt release or dissolution consistent with the release rates, which is normally obtained with the uncoated tablets or other substrates. Thus, they do not adversely impact or retard release of active ingredients from a substrate coated with them. Further, the coatings of this invention are readily dispersed and rapidly hydrated in aqueous media for application to a coating substrate, and provide elegant coatings which have all the benefits of coatings now in commercial use without the drawbacks that are common to them.

It is a common practice to coat pharmaceutical and veterinary tablets to obtain several advantages. Among these are to mask unpleasant tasting active ingredients with a barrier coat, to improve the surface characteristics of tablets to make them easier to swallow, to reduce the absorption of water or moisture which can potentially degrade the active ingredient or promote some other undesirable change in the tablet structure, and simply to make a more elegant appearing tablet.

Another very important function of a pharmaceutical or veterinary tablet coating is to improve the integrity of the tablet itself. Uncoated tablets are often subject to being abraded or chipped, causing a loss of active ingredient in the process. More dramatically, they may break into two or more pieces. One measure of a useful coating is its ability to prevent any of these physical degradations of tablet structure. The effectiveness of a coating material to prevent abrading, chipping, or breakage of the tablet is determined by friability testing.

Confectionery and foods may be coated with a formulation to preserve the confection or food from deteriorating by contact with the oxygen and the moisture in the atmosphere. Coats can provide improved appearance and desirable organoleptic properties to the food as well as preventing loss of flavor.

Animal feed may be coated to improve its flowability, appearance and its resistance to powdering or dusting. In such applications, the coating may be formulated to include vitas, hormones, antibiotics, or the like, to benefit the livestock, which will consume the feed.

Seeds may be coated to preserve the viability of the seeds by protecting against moisture. They may also be coated as a means for increasing particle size to facilitate mechanical planting. A dye can be included in the coating formulation to identify the seeds as to quality, type, or some other designation. Frequently, a pesticide, e.g., a fungicide, is incorporated into the coating formulation to protect both the seed itself and the seedling that results from germination of the seed. In all cases, this coating must not decrease the viability of the seeds or interfere with germination when the seeds are planted in the soil.

Fertilizers, in either granular or tableted forms, may be coated to retain the integrity of the form and, especially, to protect the fertilizer from moisture, which can cause agglomerates during storage, which could make rapid, even application to the soil difficult or inconvenient.

Coating of tableted pesticide formulations serves to maintain the integrity of the tablets or granules until they are placed in water where they rapidly disintegrate, forming a solution or slurry to be applied to the soil or plants. A second, and equally important, function of the coatings on tablets containing pesticides is to prevent human contact with the pesticide, thereby increasing safety for those handling and applying the pesticide.

SUMMARY OF THE INVENTION

It has been found that these and other advantages may be achieved in accordance with the present invention by a coating composition, which comprises a unique combination of materials specifically adapted for a prompt release when placed aqueous media or ingested, e.g., by a human. The coating composition of the present invention comprises sodium alginate as a primary film-former. All other prior art refer to the use of sodium alginate as a secondary film-former. A secondary film-former serves as an adjunct to a primary film-former and helps or supports the film formed by the primary film former. It has been surprisingly and unexpectedly found by the present inventors that sodium alginate could be used as a primary film former, optionally with plasticizers for coating substrates like pharmaceutical dosage forms, veterinary substrates, nutraceutical products confectionery products, fertilizers, seeds and pesticides. The coating composition of the present invention may additionally comprise detackifying agents, plasticizers, preservatives, colorants, and opacifying agents, sweetening agents and flavoring agents. The use of preservatives prevents the growth of microbes during storage of coating suspension more than 24 hours. As the present invention has only 45 minutes of hydration time, which eliminate the necessity to prepare the coating solution on prior day or before 12 hours of use. The present inventive composition can be used immediately after preparation.

More specifically, the present invention provides a prompt release, edible, hardenable coating composition comprising sodium alginate, with or without a plasticizer, a detackifying agent, and preservative in dry coatings and aqueous dispersions thereof.

The present invention provides pharmaceutical, veterinary tablet, caplets, pellets, granules, neutraceuticals, food, confectionery, seeds, animal feed, fertilizers and pesticide tablets coated with the prompt release edible, hardenable composition of this invention.

DETAILED DESCRIPTION OF THE INVENTION

For purposes of this application, the term "edible" is intended to mean food grade materials, which are approved by regulatory authorities for use in pharmaceutical or food applications. The term "hardenable" used to describe the coating compositions of this invention is intended to include only those coating compositions that are capable of being dried from an aqueous solution or dispersion thereof into a solid coating which resists abrasive forces, i.e. a hardened coating, as distinguished from those "enrobing" coatings on confections which set up into a soft coating that can be handled and packaged but which do not resist abrasive forces significantly. The terms "immediate", "rapid" or "prompt" release as applied to dissolution rates or times for the coating compositions of this invention or tablets coated with the compositions of this invention means that the coatings of this invention meet U.S. Pharmacopoeia standards (U.S.P. monograph 23) for rapid or immediate dissolution of active ingredients from tablets or other solid dosage forms coated therewith. Thus, they provide prompt release or dissolution consistent with the release rates, which is normally obtained with the uncoated tablets or other substrate. They do not, consistent with the pharmacopeia standards above, when placed in aqueous media or ingested by, e.g., a human, significantly impact or retard release or dissolution of tablets or other solid dosage forms coated therewith. For example, coatings made in accordance with the present invention are substantially or completely disintegrated and/or dissolved within less than 10 minutes after being ingested or placed in aqueous media. Thus, when a pharmaceutical solid dosage form is coated with the coating of this invention and ingested by a human or other animal, the coating of this invention is dissolved or disintegrated prior to leaving the stomach. These definitions are intended to apply throughout this application unless a contrary meaning is clearly indicated.

Sodium alginate provides film-forming characteristics required to provide an elegant coating which is particularly useful in, for example, coating pharmaceutical and veterinary tablets, caplets, granules, and spheres which contain active ingredients which require release promptly after being placed in aqueous media or ingested.

As discussed in greater detail below, the Sodium alginate preferred for use in the present invention is sodium alginate, which has an average particle size below about 100 microns, preferably sodium alginate, which has an average particle size in the range of 1 to 50 microns.

Sodium alginate is sodium salt of alginic acid. Alginic acid extracted from various species of deep-sea weed like *Phaeophyceae*. Sodium alginate is a polysaccharide, like starch and cellulose. It is composed of several building units (typically 100-3000) linked together in a flexible chain. Long molecules constructed from identical or nearly identical building units are called polymers, while the building units themselves are called monomers. Polymers of natural origin are commonly called biopolymers.

Sodium alginate is built upon the basis of two sugars, which are both uronates, the salts of mannuronic and guluronic acid. When producing alginates, uronic acid is converted into the salt-form mannuronate (M) and guluronate (G).

The G- and M-units are joined together in one of three blocks: GG . . . MM . . . , and MG . . . . The proportion, distribution, and length of these blocks determine the chemical and physical properties of the sodium alginate molecules.

The functional category to which sodium alginate is classified for its use in pharmaceuticals, include it use as a stabilizing agent, suspending agent, tablet and capsule disintegrant, tablet binder and viscosity increasing agent.

Sodium alginate has been used in a variety of oral and topical pharmaceutical formulations. I tablet formulations, sodium alginate may be used as both a binder and disintegrant; it has been used as a diluent in capsule formulations.

Sodium alginate has been used in the preparation of sustained release oral formulations since it can delay the dissolution of a drug from tablets, capsules and aqueous dispersions.

In topical formulations, sodium alginate is widely used as a thickening and suspending agent in a variety of pastes, creams and gels and as a stabilizing agent for oil-in-water emulsions. Recently, sodium alginate has been used for the aqueous microencapsulation of drugs and in the formation of nanoparticles.

The adhesiveness of hydrogels prepared from sodium alginate has been investigated and drug release from oral mucosal adhesive tablets based on sodium alginate has been reported Other novel delivery systems containing sodium alginate include an ophthalmic solution that forms a gel in-situ when administered to the eye and a freeze-dried device intended for the delivery of bone-growth factors. Hydrogel systems containing alginates have also been investigated for the delivery of proteins and peptides.

Therapeutically, sodium alginate has been used in combination with $H_2$-receptor antagonists in the management of gastroesophagel reflux and as a haemostatic in surgical dressings. Alginate dressings, used to treat exuding wounds, often contain significant amounts of sodium alginate as this improves the gelling properties. Sodium alginate is also used in food and cosmetic products.

Sodium alginate occurs as an odorless and tasteless, white to pale yellowish-brown colored powder. A 1% w/v aqueous solution has a pH of about 7.2. It is practically insoluble in ethanol, ether, chloroform and ethanol/water mixtures in which the ethanol content is greater than 30%. It is practically insoluble in other organic solvents and aqueous acidic solutions in which pH is less than 3. It is slowly soluble in water, forming a viscous colloidal solution. Various grades of sodium alginate are commercially available that yield aqueous solutions of varying viscosity. A 1% w/w aqueous solution, at 20° C., has a viscosity of 20-400 mPas (20-400 cP). Viscosity may vary depending upon concentration, pH, temperature or the presence of metal ions. Above pH 10, viscosity decreases.

Sodium alginate is a hygroscopic material, though stable if stored at low relative humidity and a cool temperature. Aqueous solutions of sodium alginate are most stable at pH 4-10. Below pH 3, alginic acid is precipitated. Alginate solutions should not be stored in metal containers.

Sodium alginate solutions are susceptible on storage to microbial spoilage, which may affect solution viscosity. Heating sodium alginate solutions to temperatures above 70° C., causes depolymerization with a loss in viscosity. Autoclaving solutions of sodium alginate can also cause a decrease in viscosity depending upon the nature of any other substances present. Gamma irradiation should not be used to sterilize sodium alginate solutions since this process severely reduces solution viscosity.

External use preparations of sodium alginate maybe preserved by addition of 0.1% chlorocresol, 0.1% chloroxylenol or parabens. Benzoic acid may also be used if the medium is acidic. The bulk material should be stored in an airtight container in a cool, dry place. Sodium alginate is generally regarded as a nontoxic and nonirritant material, although excessive oral consumption may be harmful. The WHO has not specified an acceptable daily intake for alginic acid and alginate salts, as the levels used in food do not represent a hazard to health.

The viscosity of an inventive composition solution depends on the concentration of sodium alginate and the length of the sodium alginate molecules, i.e. the number of monomer units in the chains. The longer the chains the higher the viscosity at similar concentrations. In the present invention the viscosity of sodium alginate used is between 5 to 30 cps, and most preferably below 10 cps. As the viscosity increases, subsequently the solid content will decrease in the inventive aqueous coating composition.

The inventive composition based on sodium alginate has shear-thinning characteristics, i.e. the viscosity decreases with increasing shear rate (stirrer speed). This property, is also called pseudoplasticity, or non-Newtonian flow. Standard grades of sodium alginate precipitate or form gels in acid conditions.

On dissolving the present inventive composition in water, the molecules of sodium alginate hydrate and the solution gains viscosity. The dissolved molecules are not completely flexible; rotation around the glycosidic linkages in the G-block regions is somewhat hindered, resulting in a stiffening of the chain. Solutions of stiff macromolecules are highly viscous. Temperature defines the energetic state of any chemical molecule. Hence temperature influences the response of alginates to shear forces. As a general rule, temperature increases of 1° C. lead to a viscosity drop of approximately 2.5%, Sodium Alginate is generally less susceptible to microbial attack than many other carbohydrates. A depolymerization of the polymer upon storing may occur, hence resulting in a loss of viscosity. To avoid loss of viscosity a suitable preservative such as sorbic acid, potassium sorbate, benzoic acid, sodium benzoate or esters of hydroxybenzoic acid is recommended for food applications. In industrial applications formaldehyde, sodium pentachlorophenate and other phenolic derivatives may be used.

The level of coating applied to any substrate forms is preferably between about 0.5% to about 10% by weight of the uncoated dosage form, more preferably from about 2% to about 5%, by weight of the uncoated dosage form. This level of coating will provide an elegant, serviceable coating to a wide variety of dosage forms. To apply a heavier coating to tablets would not be economical, and it might adversely affect disintegration of the tablets or other properties. Too light a coating would not provide optimal properties normally expected from a coating, for example, improved friability or adequate taste masking.

For confections the coating level should be about 5% to about 10% by weight of the uncoated confection. Seed coatings should be in the range of about 3% to about 6% by weight of the uncoated seeds. Fertilizers and pesticide tablets and granules benefit from coating of 1% to about 3%, by weight of the uncoated granules or tablets.

From the following examples it has been shown that the coatings of the present invention may be applied successfully to tablets having a wide variety of active ingredients incorporated therein. For example, it has been reported that multivitamin tablets are difficult to coat because of the lipophilic surface properties of the vitamins. Similarly, Ibuprofen is a challenging active ingredient to coat. Tablets comprising both of these difficult-to-coat active ingredients have been coated readily with the instant invention, providing elegant tablets. Additionally, the coatings have been applied to tablets, which have been debossed with letters or a logo without bridging which would hide, or even obliterate, the debossed design.

Storage of coated tablets under ambient temperature and humidity and 40° C. and 75% relative humidity for one to three months has demonstrated that no significant degradation has occurred. These tablets have disintegrated within the same length of time as the same batch of newly coated tablets did, and in each case provided dissolution rates and times substantially equal to those of the uncoated tablets used as a substrate for coating. This is an additional unexpected benefit of the coatings based on sodium alginate, and it differs from the known drawbacks of HPMC. All components of the formulation are typically pharmaceutically acceptable, edible food grade materials.

The following examples, weight gain is in percentages and tablet hardness is in Kilograms (Kg), are provided to demonstrate the method of preparation and application of these elegant coatings, but they are not intended to be limiting as to amounts and the type of optional ingredients or the specific method of application of the tablet coating described herein.

EXAMPLE 1

In a one liter, plastic beaker 270 g of DM water (pH -7) is taken and stirred with propeller stirrer of varying speed, to form a vortex. To this is added 30 g of Sodium Alginate (7 cps viscosity grade) and 4.4 g of polyethylene glycol 6000 slowly in the vortex. Slow addition to vortex eliminates the chances of lump formation. After addition of powder completely, there is an increase in the viscosity of the dispersion. The stirring is continued for about 5 minutes, wherein the viscosity then decreases and then comes back to normal. The mixture is stirred for about 45 minutes after which the dispersion is passed through a nylon cloth of # 100 mesh size to remove lumps and undissolved matter if any. This filtered dispersion of the inventive aqueous coating composition is then applied to 1000 g of placebo tablets, in 12" conventional coating pan as described below:

| | |
|---|---|
| Pan Size | 12" with 3 inbuilt baffles |
| Pan rpm | 18 |
| Inlet air temperature | 55 to 60° C. |
| Tablet Bed temperature | 34 to 40° C. |
| Prewarning | 10 to 15 minutes by inching |
| Spray Gun | Bullows 630, with 1.2 mm nozzle |
| Spray pattern | Cone shape |
| Atomization air pressure | 2.5 kg/cm$^2$ |
| Exhaust | On |
| Spray rate | 5 to 7 g/minutes |
| Total spray time | 50 minutes |
| Post drying | 10 to 15 minutes by inching |

The coated tablets had a glossy appearance. The total weight of tablets after coating was 1020 g, i.e. 2% actual weight gain achieved on the tablets.

The average initial hardness of coated placebo tablets was 5.0 kg, friability of these coated tablets was 0% after 100 rotations, and disintegration time was less than 3 minutes in deionized water at 37° C. After one month of storage at room temperature and at 40° C. and 75%, hardness was more than 4.5 Kg, and disintegration time was less than three minutes, for both the storage conditions. After two months storage at room temperature and at 40° C. and 75%, hardness was more these conditions, hardness was more than 4.5 Kg, and disintegration time was less than three minutes, for both the storage conditions. Example 2 gives a representative formula of the dry components illustrative of the invention and are all weight in percent by dry weight.

EXAMPLE 2

| Sr. No. | Ingredient | Percentage (w/w) | Quantity taken (grams) |
|---|---|---|---|
| 1. | Sodium alginate 30 cps | 30 | 300.00 |
| 2. | Polyethylene glycol 6000 | 4.4 | 44.00 |
| 3. | Talc | 40 | 400.00 |
| 4. | Titanium dioxide | 25 | 250.00 |
| 5. | Sodium benzoate | 0.1 | 1.00 |
| 6. | Methyl parabens | 0.5 | 5.00 |
| | TOTAL | 100 | 1000.00 |

In laboratory rapid mixer 300 g of sodium alginate 30 cps (Snap, India), 44 g of polyethylene glycol 6000 powder (Clarient GmbH, Germany), 400 g of Talc powder (Golcha, India), 250 g of Titanium Dioxide (Agrofert holdings, Zech Republic), 1.0 g of Sodium benzoate & 5.0 g of methyl parabens (Qualigen, India) was taken. This dry blend was mixed for 3 cycles of 30 seconds each. The resultant dry mix powder was then passed through #60 mesh screen.

In a 2 liter capacity plastic beaker 970 g of DM water (pH -7) is taken and stirred with propeller stirrer of varying speed, to form a vortex. To this is added 30 g of inventive composition of example 2. Dispersion is prepared and coated on placebo tablets as per example 1.

EXAMPLE 3

| Sr. No. | Ingredient | Percentage (w/w) | Quantity taken (grams) |
|---|---|---|---|
| 1. | Sodium alginate 15 cps | 30 | 300.00 |
| 2. | Polyethylene glycol 6000 | 4.4 | 44.00 |
| 3. | Talc | 40 | 400.00 |
| 4. | Titanium dioxide | 25 | 250.00 |
| 5. | Sodium benzoate | 0.1 | 1.00 |
| 6. | Methyl parabens | 0.5 | 5.00 |
| | TOTAL | 100 | 1000.00 |

The inventive composition prepared as per procedure in example 2. In a one liter capacitty plastic beaker 570 g of DM water (pH -7) is taken and stirred with propeller stirrer of varying speed, to form a vortex. To this is added 30 g of inventive composition of example 3. Dispersion is prepared and coated on placebo tablets as per example 1.

EXAMPLE 4

| Sr. No. | Ingredient | Percentage (w/w) | Quantity taken (grams) |
|---|---|---|---|
| 1. | Sodium alginate 5 cps | 30 | 300.00 |
| 2. | Polyethylene glycol 6000 | 4.4 | 44.00 |
| 3. | Talc | 40 | 400.00 |

-continued

| Sr. No. | Ingredient | Percentage (w/w) | Quantity taken (grams) |
|---|---|---|---|
| 4. | Titanium dioxide | 25 | 250.00 |
| 5. | Sodium benzoate | 0.1 | 1.00 |
| 6. | Methyl parabens | 0.5 | 5.00 |
|  | TOTAL | 100 | 1000.00 |

The inventive composition prepared as per procedure in example 2. In a one liter capacity, plastic beaker 130 g of DM water (pH -7) is taken and stirred with propeller stirrer of varying speed, to form a vortex. To this is added 30 g of inventive composition of example 4. Dispersion is prepared and coated on placebo tablets as per example 1.

EXAMPLE 5

| Sr. No. | Ingredient | Percentage (w/w) | Quantity taken (grams) |
|---|---|---|---|
| 1. | Sodium alginate 7 cps | 30 | 300.00 |
| 2: | Polyethylene glycol 6000 | 4.4 | 44.00 |
| 3. | Talc | 40 | 400.00 |
| 4. | Titanium dioxide | 25 | 250.00 |
| 5. | Sodium benzoate | 0.1 | 1.00 |
| 6. | Methyl parabens | 0.5 | 5.00 |
|  | TOTAL | 100 | 1000.00 |

In laboratory rapid mixer 300 g of sodium alginate 7 cps (Snap, India), 44 g of polyethylene glycol 6000 powder (Clarient GmbH, Germany), 400 g of Talc powder (Golcha, India), 250 g of Titanium Dioxide (Agrofert holdings, Zech Republic), 1.0 g of Sodium benzoate & 5.0 g of methyl parabens (Qualigen, India) was taken. This dry blend was mixed for 3 cycles of 30 seconds each. The resultant dry mix powder was then passed through # 60 mesh screen. 50 g of this inventive composition was taken for coating Ibuprofen 200 mg tablets. In a one liter, plastic beaker 300 g of DM water (pH -7) is taken and stirred with propeller stirrer of varying speed, to form a vortex. To this is added 50 g inventive composition slowly in the vortex to avoid the chances the chances of lump formation. The mixture is stirred for about 45 minutes and passed through nylon cloth of # 100 mesh size to ensure removal of lumps if any and obtain a smooth coating solution. The inventive aqueous coating composition then applied to 1500 g of Ibuprofen tablets 200 mg, in 12" conventional coating pan as described bellow:

| | |
|---|---|
| Pan Size | 12" with 3 inbuilt baffles |
| Pan rpm | 18 |
| Inlet air temperature | 45 to 50° C. |
| Tablet Bed temperature | 30 to 34° C. |
| Prewarning | 10 to 15 minutes by inching |
| Spray Gun | Bullows 630, with 1.2 mm nozzle |
| Spray pattern | cone shape |
| Atomization air pressure | 2.5 kg/cm$^2$ |
| Exhaust | on |
| Spray rate | 5 to 7 g/minutes |
| Total spray time | 50 minutes |
| Post drying | 10 to 15 minutes by inching |

Coated tablets were white, glossy appearance. The total weight of tablets after coating was 1530.0 g, i.e. 2% actual weight gain achieved on the tablets.

The average initial hardness of coated Ibuprofen tablets 200 mg was 7.0 kg. Friability of these coated tablets was 0% after 4 minutes, and disintegration time was less than 5 minutes in deionized water at 37° C. After two months of storage at room temperature, hardness was at about 6.5 Kg, and disintegration time was less than five minutes. Tablets stored for two months at 40° C. and 75% relative humidity had hardness of 6.6 Kg and a disintegration time of less than 5 minutes.

The examples given below illustrate the invention, all percentages by weight. In Examples 6-15, the components of each formulation are mixed together, formed into a coating solution and applied to placebo tablets as described in examples 1 to 4, to obtain tablets coated with sodium alginate as a primary film-former.

EXAMPLE 6

| Sr. No. | Ingredient | Percentage (w/w) | Quantity taken (grams) |
|---|---|---|---|
| 1. | Propylene glycol alginate | 30 | 300.00 |
| 2. | Polyethylene glycol 6000 | 4.4 | 44.00 |
| 3. | Talc | 40 | 400.00 |
| 4. | Titanium dioxide | 25 | 250.00 |
| 5. | Sodium benzoate | 0.1 | 1.00 |
| 6. | Methyl parabens | 0.5 | 5.00 |
|  | TOTAL | 100 | 1000.00 |

EXAMPLE 7

| Sr. No. | Ingredient | Percentage (w/w) | Quantity taken (grams) |
|---|---|---|---|
| 1. | Sodium alginate 7 cps | 35 | 350.00 |
| 2. | Polyethylene glycol 6000 | 4.4 | 44.00 |
| 3. | Talc | 35 | 350.00 |
| 4. | Titanium dioxide | 25 | 250.00 |
| 5. | Sodium benzoate | 0.1 | 1.00 |
| 6. | Methyl parabens | 0.5 | 5.00 |
|  | TOTAL | 100 | 1000.00 |

EXAMPLE 8

| Sr. No. | Ingredient | Percentage (w/w) | Quantity taken (grams) |
|---|---|---|---|
| 1. | Sodium alginate 7 cps | 40 | 400.00 |
| 2. | Polyethylene glycol 6000 | 4.4 | 44.00 |
| 3. | Talc | 30 | 300.00 |
| 4. | Titanium dioxide | 25 | 250.00 |
| 5. | Sodium benzoate | 0.1 | 1.00 |
| 6. | Methyl parabens | 0.5 | 5.00 |
|  | TOTAL | 100 | 1000.00 |

EXAMPLE 9

| Sr. No. | Ingredient | Percentage (w/w) | Quantity taken (grams) |
|---|---|---|---|
| 1. | Sodium alginate 7 cps | 30 | 300.00 |
| 2. | Triacetin | 4.4 | 44.00 |
| 3. | Talc | 40 | 400.00 |
| 4. | Titanium dioxide | 10 | 100.00 |
| 5. | Sodium benzoate | 0.1 | 1.00 |
| 6. | Methyl parabens | 0.5 | 5.00 |
| 7. | Lake Quinoline yellow | 15 | 150.00 |
|  | TOTAL | 100 | 1000.00 |

EXAMPLE 10

| Sr. No. | Ingredient | Percentage (w/w) | Quantity taken (grams) |
|---|---|---|---|
| 1. | Sodium alginate 7 cps | 30 | 300.00 |
| 2. | Propylene Glycol | 4.4 | 44.00 |
| 3. | Talc | 40 | 400.00 |
| 4. | Titanium dioxide | 10 | 100.00 |
| 5. | Sodium benzoate | 0.1 | 1.00 |
| 6. | Methyl parabens | 0.5 | 5.00 |
| 7. | Lake carmosine | 15 | 150.00 |
|  | TOTAL | 100 | 1000.00 |

EXAMPLE 11

| Sr. No. | Ingredient | Percentage (w/w) | Quantity taken (grams) |
|---|---|---|---|
| 1. | Sodium alginate 7 cps | 30 | 300.00 |
| 2. | Polyethylene glycol 6000 | 4.4 | 44.00 |
| 3. | Talc | 40 | 400.00 |
| 4. | Titanium dioxide | 25 | 250.00 |
| 5. | Sodium benzoate | 0.6 | 6.00 |
|  | TOTAL | 100 | 1000.00 |

EXAMPLE 12

| Sr. No. | Ingredient | Percentage (w/w) | Quantity taken (grams) |
|---|---|---|---|
| 1. | Sodium alginate 7 cps | 80 | 800.00 |
| 2. | Polyethylene glycol 6000 | 20 | 200.00 |
|  | TOTAL | 100 | 1000.00 |

EXAMPLE 13

| Sr. No. | Ingredient | Percentage (w/w) | Quantity taken (grams) |
|---|---|---|---|
| 1. | Sodium alginate 7 cps | 30 | 300.00 |
| 2. | Triacetin | 4.5 | 45.00 |
| 3. | Talc | 40 | 400.00 |
| 4. | Titanium dioxide | 15 | 150.00 |
| 5. | Vanilla Flavour | 10 | 100.00 |
| 6. | Methyl parabens | 0.5 | 5.00 |
|  | TOTAL | 100 | 1000.00 |

EXAMPLE 14

| Sr. No. | Ingredient | Percentage (w/w) | Quantity taken (grams) |
|---|---|---|---|
| 1. | Sodium alginate 7 cps | 30 | 300.00 |
| 2. | Polyethylene glycol 6000 | 4.4 | 44.00 |
| 3. | Talc | 30.6 | 306.00 |
| 4. | Titanium dioxide | 14 | 140.00 |
| 5. | Red Iron Oxide | 10 | 100.00 |
| 6. | Methyl parabens | 0.5 | 5.00 |
| 7. | Chocolate Flavour | 10 | 100.00 |
| 8. | Sodium saccharine | 0.5 | 5.00 |
|  | TOTAL | 100 | 1000.00 |

EXAMPLE 15

| Sr. No. | Ingredient | Percentage (w/w) | Quantity taken (grams) |
|---|---|---|---|
| 1. | Sodium alginate 7 cps | 75 | 750.00 |
| 2. | Triacetin | 4.4 | 44.00 |
| 3. | Aspartame | 20 | 200.00 |
| 4. | Sodium benzoate | 0.6 | 6.00 |
|  | TOTAL | 100 | 1000.00 |

The viscosities of the reconstituted dispersions exemplified by way of the above examples was recorded on a Brookfield viscometer and it was found that they ranged from 36 cps to 5000 cps.

While the invention has been described in detail and with reference to specific embodiments thereof, it will be apparent to one skilled in the art that various changes and modifications can be made therein without departing from the spirit and scope thereof.

We claim:
1. A dry film coating composition, comprising:
sodium alginate in the range of 5 to 95% by weight of the composition and preservative, and
optionally, detackifying agent, plasticizer, opacifier, colorant(s), or mixture thereof;
wherein:
the composition is substantially free of synthetic cellulosic polymer and gelatin;
the composition is suitable for forming a film coating dispersion for film coating substrates including pharma- ceutical, veterinary, nutraceutical, confectionery, seed, fertilizer, animal feed, or fertilizer substrate products.

2. The composition of claim 1, comprising sodium alginate at about 10 to 60% by weight of the composition.

3. The composition of claim 1, wherein the sodium alginate has a viscosity of about 5 cps to 30 cps.

4. The composition of claim 1, comprising plasticizer, wherein the plasticizer is selected from the group consisting of polyethylene glycol, polyethylene glycol derivatives, triacetin, dibutyl sebacate, diethyl phthalate, propylene glycol, glycerin, liquid paraffin, triethyl citrate, and mixtures thereof.

5. The composition of claim 1, comprising plasticizer in the range of 1 to 25% by weight of the composition.

6. The composition of claim 5, wherein the plasticizer comprises polyethylene glycol having a molecular weight of about 200 to 20,000.

7. The composition of claim 5, the plasticizer being triacetin.

8. The composition of claim 1, comprising detackifying agent, wherein the detackifying agent comprises talc, colloidal silicon dioxide, stearic acid, salts of stearic acid, calcium chloride, calcium carbonate, dicalcium phosphate, starch, maltodextrin, lactose, microcrystalline cellulose, mannitol, or combinations thereof.

9. The composition of claim 8, comprising detackifying agent at about 5 to 90% by weight of the composition.

10. The composition of claim 1, comprising preservative at about 0 to 3% by weight of the composition.

11. The composition of claim 1, comprising colorant or opacifier, wherein the colorant/opacifier comprises dyes, natural colors, lake colors, oxide colors, or combinations thereof.

12. The composition of claim 11, comprising colorant/opacifier at about 0 to 80% by weight of the composition.

13. The composition of claim 1, further comprising a sweetening agent being natural sugars, inverted sugars, artificial sweetening agents, sodium saccharine, or combinations thereof.

14. The composition of claim 13, comprising sweetening agent at about 0 to 30% by weight of the composition.

15. The composition of claim 1, further comprising a flavoring agent(s) at about 0 to 20% by weight of the composition.

16. The composition of claim 1, having solids content from about 2 weight percent to about 20 weight percent.

17. A method of making aqueous coating composition in water by adding and stirring the inventive composition of claim 1, to achieve uniform, homogeneous, consistent, lump free, colored or colorless dispersion.

18. The composition of claim 1, wherein the composition consists essentially of:
sodium alginate in the range of 5 to 95% by weight of the composition, plasticizer, and preservative, and
optionally, detackifying agent, opacifier, colorant, or mixture thereof.

19. The composition of claim 1, wherein the composition consists of:
sodium alginate in the range of 5 to 95% by weight of the composition, plasticizer, and preservative, and
optionally, detackifying agent, opacifier, colorant, or mixture thereof.

20. The composition of claim 1, wherein film former consists of sodium alginate.

21. An aqueous dispersion of a composition comprising:
sodium alginate which has shear thinning viscosity in the range of about 5 cps to 30 cps, sodium alginate being in range of 0.1 to 30% by weight of liquid composition;
a plasticizer selected from the group consisting of polyethylene glycol, triacetin, dibutyl sebacate, propylene glycol, glycerin, triethyl citrate and mixtures thereof;
further comprising a detackifying agent selected from the group consisting of talcum, colloidal silicon dioxide, stearic acid, salt of stearic acid, calcium chloride, calcium carbonate, dicalcium phosphate, starch maltodextrin, lactose, and mannitol;
a preservative selected from group of sorbic acid, sodium benzoate, sodium propionate, potassium sorbate, methyl parabens, propyl parabens, and
opacifier(s)/colorant(s) selected from the group consisting of titanium dioxide, dyes, natural colors, lake colors, and oxide colours;
wherein:
the composition is substantially free of synthetic cellulosic polymer and gelatin.

22. An edible, hardenable, prompt release pharmaceutical and veterinary coating composition comprising a dry blend of sodium alginate and plasticizer, the sodium alginate being in the range of about 5% to 95% by weight of composition, and optionally a detackifying agent, preservative, opacifiers and colorants, wherein said coating composition does not, when ingested or placed in an aqueous medium, significantly retard release or active ingredients from a pharmaceutical and veterinary solid dosage form to which said coating is applied;
wherein:
the composition is substantially free of synthetic cellulosic polymer and gelatin.

23. A pharmaceutical and veterinary tablet, caplets, pellets, granules, nutraceuticals, food, confectionery, seeds, animal feed, fertilizers and pesticide tablets, coated with the coating composition of claim 22.

* * * * *

(12) EX PARTE REEXAMINATION CERTIFICATE (10107th)
United States Patent
Rajsharad et al.

(10) Number: US 8,123,849 C1
(45) Certificate Issued: Apr. 9, 2014

(54) AQUEOUS FILM COATING COMPOSITION CONTAINING SODIUM ALGINATE AND PREPARATION THEREOF

(75) Inventors: Chetan Rajsharad, Mumbai (IN); Shivaji Kamble, Mumbai (IN); Suresh Pareek, Mumbai (IN)

(73) Assignee: Ideal Cures Pvt. Ltd., Mumbai, Maharashtra (IN)

Reexamination Request:
No. 90/012,288, May 29, 2012

Reexamination Certificate for:
Patent No.: 8,123,849
Issued: Feb. 28, 2012
Appl. No.: 12/095,412
Filed: May 29, 2008

(21) Appl. No.: 90/012,288

(22) PCT Filed: Jan. 31, 2006

(86) PCT No.: PCT/IN2006/000034
§ 371 (c)(1),
(2), (4) Date: May 29, 2008

(87) PCT Pub. No.: WO2007/063553
PCT Pub. Date: Jun. 7, 2007

(30) Foreign Application Priority Data

Nov. 29, 2005 (IN) .......................... 1479/MUM/2005

(51) Int. Cl.
*C09D 105/04* (2006.01)
*C08L 5/04* (2006.01)
*A61K 9/34* (2006.01)
*A61K 9/28* (2006.01)
*C08L 71/02* (2006.01)
*C08K 5/00* (2006.01)

(52) U.S. Cl.
CPC ................. *A61K 9/286* (2013.01); *C08L 71/02* (2013.01); *C08K 5/0016* (2013.01); *C08K 5/0058* (2013.01)
USPC .................. 106/205.01; 106/205.72; 424/464; 424/485

(58) Field of Classification Search
None
See application file for complete search history.

(56) References Cited

To view the complete listing of prior art documents cited during the proceeding for Reexamination Control Number 90/012,288, please refer to the USPTO's public Patent Application Information Retrieval (PAIR) system under the Display References tab.

*Primary Examiner* — Ling Xu

(57) ABSTRACT

A coating composition comprising sodium alginate and plasticizer, optionally detackifying agents, opacifers and colorants. The coating composition of the present invention may be applied to a pharmaceutical and veterinary tablet, caplets, pellets, granules, neutraceuticals, food, confectionery, seeds, animal feed, fertilizers and pesticide tablets and provides an elegant, glossy, prompt release coating which does not retard the release of active ingredients from the coated substrate.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-23 are cancelled.

\* \* \* \* \*